United States Patent [19]

Williams

[11] Patent Number: 5,221,772

[45] Date of Patent: Jun. 22, 1993

[54] PREPARATION OF 2-HYDROXYPHENYL-ACETIC ACID

[75] Inventor: Alfred G. Williams, Binfield, England

[73] Assignee: Imperial Chemical Industries PLC, London, Great Britain

[21] Appl. No.: 710,730

[22] Filed: Jun. 4, 1991

[51] Int. Cl.⁵ .............................................. C07C 65/01
[52] U.S. Cl. .................................................... 562/478
[58] Field of Search ......................................... 562/478

[56] References Cited

FOREIGN PATENT DOCUMENTS

| | | |
|---|---|---|
| 2040643 | 2/1972 | Fed. Rep. of Germany . |
| 57-135049 | 2/1981 | Japan . |
| 57-185234 | 11/1982 | Japan . |
| 58-206541 | 12/1983 | Japan . |
| 90/09976 | 9/1990 | PCT Int'l Appl. . |
| 2083023 | 3/1982 | United Kingdom . |

OTHER PUBLICATIONS

Noller C. R. "Chem of Organic Cmpds" W. B. Saunders Company Oct. 1960 p. 510.
Chem. Ber. (1920), 53, p. 2230.
Chem. Ber (1905), 38, pp. 2121-2126.
J. Am. Chem. Soc., vol. 45, pp. 1906-1916.
J. Chem. Soc., (1929), pp. 1870-1873 (Chem. Abs., vol. 24 p. 77).
J. Chem. Soc. (1927), pp. 113-1122.
Zh. Org. Khim (1971), vol. 7, part 12, pp. 2567-2569 (Chem. Abs. 76 72171Y).

*Primary Examiner*—Paul J. Killos
*Attorney, Agent, or Firm*—Lynn Marcus-Wyner

[57] ABSTRACT

A process for the preparation of:

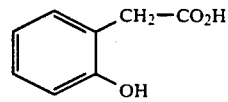

the process comprising treating (2-chlorophenyl)acetic acid with an alkali metal hydroxide (for example, sodium hydroxide) in an organic solvent (for example, an inert hydrocarbon solvent), in the presence of a catalyst (for example a copper salt) at a temperature above 130° C. (for example in the range 130° C. to 300° C.).

8 Claims, No Drawings

PREPARATION OF 2-HYDROXYPHENYL-ACETIC ACID

The present invention relates to a process for the preparation of (2-hydroxyphenyl)acetic acid.

A process for preparing (2-hydroxyphenyl)acetic acid from (2-chlorophenyl)acetic acid is disclosed in DE-OLS-2040643. The process disclosed uses water as solvent and has to be carried out in an autoclave. The catalyst that must be used in this process is a mixture of copper metal and a copper salt.

Methods disclosed in GB2083023, J57185234, J57135049, J58206541, Chem. Ber. (1905) 38 2121, DE-288116 and Chem. Ber. (1920) 53 2230 also show the conversion of (2-chlorophenyl)acetic acids to (2-hydroxyphenyl)acetic acids. All of the above methods require an autoclave or similar pressure vessel.

According to the present invention there is provided a process for the preparation of (2-hydroxyphenyl)acetic acid, the process comprising treating (2-chlorophenyl)acetic acid with an alkali metal hydroxide in an organic solvent, in the presence of a suitable catalyst at a temperature above 130° C.

The alkali metal hydroxide is, for example, potassium hydroxide, but is preferably sodium hydroxide, for example sodium hydroxide in the form of pearls (available from Hayes) or in the form of crushed pellets.

Suitable catalysts include copper salts for example copper sulphate (in anhydrous or hydrated form), copper oxide, copper chloride or copper salts of organic acids.

The organic solvent has a boiling point above 130° C. preferably in the range of 150° C. to 300° C. and is preferably an inert hydrocarbon solvent. The inert hydrocarbon solvent is preferably a liquid at 10° C., more preferably a liquid at 0° C. The inert hydrocarbon solvent is even more preferably a petroleum distillation fraction, for example, 'SOLVESSO' 150 or 200 (available from ESSO), 'Isopar M' or odourless kerosene. ('SOLVESSO' and 'Isopar M' are Trade Names or Trade Marks).

The suitable temperature is above 130° C., for example in the range 130°-300° C. (preferably 150°-300° C.), but is more preferably in the range 160°-220° C., (for example, 160°-200° C.).

It is preferred that the process of the present invention is carried out at atmospheric pressure.

The process of the invention is conveniently carried out by suspending an alkali metal hydroxide in an organic solvent and adding (2-chlorophenyl)acetic acid and a catalyst to this suspension. The reaction mixture is heated to a temperature above 130° C. The reaction can be followed by a chromatographic technique for (example gas/liquid chromatography or high pressure liquid chromatography (using reverse phase medium)) to follow its progress. When the reaction is complete the mixture is cooled and water is added to it. After washing the aqueous phase with a suitable solvent (for example, hexane) it is acidified and extracted with a suitable solvent (for example, ethyl acetate). The extracts are combined, dried and evaporated to leave crude (2-hydroxyphenyl)acetic acid which may be purified.

The following Examples illustrate the process of the present invention. Where shown, NMR data are selective. No attempt is made to list every absorption. In the Examples the following abbreviations are used:
DMSO = dimethylsulphoxide
m = multiplet
s = singlet
brs = broad singlet

EXAMPLE 1

Solid pearl sodium hydroxide (as discrete spheres) (24 g) was suspended in 'SOLVESSO' 200 (100 ml) at 25° C. (2-Chlorophenyl)acetic acid (17.0 g) was added to this in one portion and the mixture was stirred for 20 minutes at room temperature after which time copper sulphate pentahydrate (1.0 g) was added. The reaction mixture was then heated and stirred at 180° C. After 15 hours gas/liquid chromatography indicated that all the (2-chlorophenyl)acetic acid had been consumed. The reaction mixture was cooled to room temperature and during this process it thickened. (The pearl sodium hydroxide was still in discrete spheres). The reaction mixture was filtered and the residue washed twice with hexane. After briefly air drying the residue, it was dissolved in water. The water solution was filtered to remove some brown solid before being washed with ethyl acetate. Charcoal was then added to the water solution and the resulting mixture was filtered through 'Hyflo' ('Hyflo' is a Trade Name of Trade Mark). The filtrate was acidified to pH 3.5 and a few oily specs were formed. These were filtered off. The resulting filtrate was extracted with ethyl acetate. The extracts were combined, dried and evaporated to give a crude product (10.5 g). The crude product was recrystallised from water and then recrystallised from acetic acid to give 2.7 g of (2-hydroxyphenyl)acetic acid as a crystalline solid (melting point 141.4°-142° C.) (theoretical m.pt. 147°-149° C.).

The following data was generated from a different preparation coming within the present invention.

Mass spectrum gave a molecular ion M+ of 152.

Proton NMR: $CH_2$ singlet at 3.4 ppm aromatic multiplet 6.7 ppm-7.0 ppm

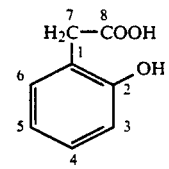

$C^{13}$NMR

| Carbon No. | ppm |
| --- | --- |
| 1 | 121.9 |
| 2 | 155.4 |
| 3 | 114.8 |
| 4 | 127.8 |
| 5 | 118.7 |
| 6 | 131.1 |
| 7 | 35.4 |
| 8 | 172.8 |

EXAMPLE 2

(2-Chlorophenyl)acetic acid (3.4 g, 0.02M), crushed sodium hydroxide pellets (4.8 g, 0.12M) and 'SOLVESSO' 200 (30 g) were stirred for 0.5 hours. Cupric sulphate pentahydrate (0.2 g, 0.0008M) was added and the mixture heated at 190°-196° C. for about 4 hours. The reaction mass was cooled to 20° C. and treated with water (50 g), transferred to a separator with a further amount of water (50 g) and filtered. The separated aqueous filtrates were acidified to about pH4 using 36% hydrochloric acid and the product was extracted into ethyl acetate (180 g). (2-Hydroxyphenyl)acetic acid (2.62 g) was isolated as a solid by distillation of the ethyl acetate.

$^1$H NMR [DMSO (d6), 250 MHz]: $\delta$3.46(2H,s); 6.7-7.2(4H,m); 9.4(1H,brs); 12.2(1H,brs) ppm.

EXAMPLE 3

'Isopar M' (500 ml), (2-chlorophenyl)acetic acid (51.3 g, 0.3M), copper II sulphate hexahydrate (2.88 g, 10 mM) and sodium hydroxide pellets (84 g, 2.1M) were changed to a 1.5 litre hastalloy vessel equipped with a stirrer and condenser. The temperature of the vessel was increased from ambient using an oil bath, while stirring the reaction mixture. The oil bath was maintained at between 210° C. and 220° C. for 6 hours and then heating was ceased and the vessel was allowed to cool to ambient temperature. Water (500 ml) was added (exothern) and the reaction mixture was stirred for a further 30 minutes. After filtering off some insoluble material (about 600 mg) the phases were separated and the upper organic phase set aside (480-490 ml). The aqueous phase was acidified to pH1 (by test paper) by adding 36% hydrochloric acid (125-155 ml, exothern), and then extracted with isopropyl acetate (2×250 ml). The combined isopropyl acetate extracts were evaporated at 60° C. and about 20 mm Hg on a rotary evaporator to give (2-hydroxyphenyl)acetic acid as brown solid (44-45 g, purity by gas chromatography 94-99%, yield 93-96%).

CHEMICAL FORMULAE
(in description)

(2-Hydroxyphenyl)acetic acid

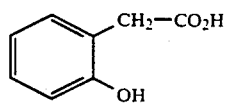

(2-Chlorophenyl)acetic acid

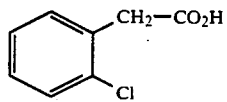

I claim:
1. A process for the preparation of (2-hydroxyphenyl)acetic acid, the process comprising treating (2-chlorophenyl)acetic acid with an alkali metal hydroxide in an organic solvent, in the presence of a copper salt at a temperature above 130° C.
2. A process as claimed in claim wherein the temperature is in the range 130° C. to 300° C.
3. A process as claimed in claim 1 wherein the organic solvent is an inert hydrocarbon solvent.
4. A process as claimed in claim 2 wherein the temperature in the range of 160° C. to 220° C.
5. A process as claimed in claim 3 wherein the organic solvent is an inert hydrocarbon solvent which is a liquid at 10° C.
6. A process as claimed in claim 1 wherein the process is carried out at atmospheric pressure.
7. A process as claimed in claim 1 wherein the copper salt may be selected from the group consisting of copper sulphate, copper oxide, copper chloride and copper salts of organic acids.
8. A process as claimed in claim 7 wherein the copper salt is copper sulphate.

* * * * *